United States Patent
Klemm

(10) Patent No.: US 9,044,193 B2
(45) Date of Patent: Jun. 2, 2015

(54) MEDICAL DEVICE

(75) Inventor: Peter Klemm, Hanau (DE)

(73) Assignee: Siemens Aktiengesellschaft, München (DE)

( * ) Notice: Subject to any disclaimer, the term of this patent is extended or adjusted under 35 U.S.C. 154(b) by 641 days.

(21) Appl. No.: 13/332,252

(22) Filed: Dec. 20, 2011

(65) Prior Publication Data

US 2012/0325611 A1 Dec. 27, 2012

(30) Foreign Application Priority Data

Dec. 21, 2010 (DE) .................. 10 2010 063 807

(51) Int. Cl.
| | | |
|---|---|---|
| *H05G 1/02* | (2006.01) | |
| *A61B 6/00* | (2006.01) | |
| *A61B 6/10* | (2006.01) | |
| *F16D 7/04* | (2006.01) | |

(52) U.S. Cl.
CPC ................ *A61B 6/4441* (2013.01); *H05G 1/02* (2013.01); *A61B 6/102* (2013.01); *A61B 6/10* (2013.01); *F16D 7/046* (2013.01)

(58) Field of Classification Search
CPC ............. A61B 6/10; A61B 6/102; H05G 1/02
USPC ............................ 378/197; 192/56.62; 464/38
See application file for complete search history.

(56) References Cited

U.S. PATENT DOCUMENTS

| | | | | |
|---|---|---|---|---|
| 3,722,644 A | * | 3/1973 | Steinhagen ................. | 192/56.57 |
| 3,889,491 A | * | 6/1975 | Wanner et al. .................. | 464/36 |
| 4,821,727 A | * | 4/1989 | Levene et al. ................. | 600/407 |
| 6,206,784 B1 | | 3/2001 | Kato | |
| 2009/0143146 A1 | * | 6/2009 | Standar ........................... | 464/36 |
| 2012/0325611 A1 | * | 12/2012 | Klemm ........................ | 192/56.1 |

FOREIGN PATENT DOCUMENTS

| | | |
|---|---|---|
| CN | 201929967 U | 8/2011 |
| DE | 82 14 297 U1 | 10/1982 |
| DE | 195 22 357 A1 | 1/1997 |
| DE | 10 2007 057 287 A1 | 6/2009 |

OTHER PUBLICATIONS

German Office Action dated Aug. 17, 2011 for corresponding German Patent Application No. DE 10 2010 063 807.2 with English translation.
Chinese Office Action dated Oct. 23, 2014 for corresponding Chinese Patent Application No. 201110432173.7 with English translation.

* cited by examiner

*Primary Examiner* — Thomas R Artman
(74) *Attorney, Agent, or Firm* — Lempia Summerfield Katz LLC

(57) ABSTRACT

A medical device having at least one electric drive for positioning at least one position-varying device segment is provided. At least one gear unit and an overload clutch are arranged along at least one mechanical drive chain between the at least one electric drive and the at least one position-varying device segment. Snap-in elements are arranged on a clutch segment of the overload clutch. The snap-in elements engage in snap-in receptacles of another clutch segment of the overload clutch. The snap-in elements and the associated snap-in receptacles are distributed irregularly.

18 Claims, 4 Drawing Sheets

MEDICAL DEVICE

This application claims the benefit of DE 10 2010 063 807.2, filed on Dec. 21, 2010.

BACKGROUND

The present embodiments relate to a medical device.

The term "medical device" relates, for example, to an X-ray device having a patient couch and a C-arm, on which an X-ray source and an X-ray detector are arranged. For safety reasons in medical devices of this type, an overload clutch is provided in a drive train. The overload clutch decouples the load (e.g., the C-arm) from the electric drive in the event of an overload, as a result of which a further movement of the load is prevented. The overload clutch may be used, for example, if an obstacle is located in the operating space of the C-arm. As a result, an adjustment movement of the C-arm is stopped. In this case, the overload clutch interrupts the drive force and/or drive torque transmitted from the electric drive via the drive train and the gear unit. As a result, the load is decoupled from the drive. Overload clutches of this type are known and may include two clutch segments that engage with one another in a force-fit fashion. During normal operation, the two clutch segments are connected to one another in a force-fit fashion and in the event of an overload, the two clutch segments are brought into a decoupled state.

An overload clutch that is configured slightly differently is known from DE 195 22 357 A1. A medical device that includes a device part that may be adjusted using a motor (e.g., a C-arm) is provided. A relative displacement that occurs between two components in the event of an overload is detected by sensors. As a result, a switch and an electric drive are switched off. In the interests of even higher operational safety, it is desirable for the load (e.g., the C-arm) to not only be electrically decoupled but also mechanically decoupled from the drive in the event of an overload.

SUMMARY AND DESCRIPTION

Conventional medical devices that include a mechanical overload clutch are designed such that the position-varying device segment may be manually moved back from the decoupled state into the coupled state following an overload. In practice, a comparably high force or a high torque is needed for this purpose. The force or the torque is essentially just as high as the force and/or torque that are needed for the decoupling of the clutch segments in the event of the overload. In some circumstances, it is difficult for the user to put the position-varying device segment back into an initial state following an overload. In the initial state, the clutch segments engage in one another in the correct relative position with respect to one another.

The present embodiments may obviate one or more of the drawbacks or limitations in the related art. For example, a medical device that may be easily returned manually to an initial state following an overload is provided.

In one embodiment, snap-in elements are arranged on a clutch segment of an overload clutch. The snap-in elements engage in snap-in receptacles of the other clutch segment of the overload clutch. The snap-in elements and the associated snap-in receptacles are distributed irregularly.

The force and/or torque that is to be expended in order to move the position-varying device segment following an overload so as to re-engage the decoupled clutch segments in one another, is dependent on the number of engaging snap-in elements and snap-in receptacles. Since the snap-in elements, which are arranged on a clutch segment, and the snap-in receptacles, which are arranged on the other clutch segment, are distributed irregularly in the initial state, if the position-varying device segment assumes the correct relative position with respect to the drive, all snap-in elements engage in the associated snap-in receptacles. Following an overload, the irregular distribution of the snap-in elements and the snap-in receptacles results in only some of the snap-in elements engaging in the snap-in receptacles. Accordingly, the twisted or displaced position-varying device segment may subsequently be returned to the initial state with a minimal force and/or a minimal torque, since only the resistance of the engaging snap-in elements is to be overcome. The force and/or torque, which is to be expended in order to return the position-varying device segment to the initial state, is always less than the force and/or torque, by which the overload clutch was activated and decoupled. As a result, the overload clutch has a switching performance that depends on the relative position of the two clutch segments.

A further embodiment related to the switching performance may be provided with the medical device if the snap-in elements and the snap-in receptacles are arranged at prime number positions distributed across the periphery. The term "periphery" may relate to the clutch segment that includes the snap-in elements. The arrangement at prime number positions provides that the individual snap-in elements and snap-in receptacles are arranged at different angular positions of the clutch segment. The distance between two adjacent snap-in elements and/or snap-in receptacles may also be different in the peripheral direction. This irregular arrangement of the snap-in elements results in the snap-in elements being rotated relative to the snap-in receptacles in the event of an overload, until the snap-in elements and the snap-in receptacles engage in the next position (e.g., until the clutch segment having the snap-in elements has covered a distance that corresponds to a space between two snap-in receptacles). In this state, only one part of the snap-in elements engages in the snap-in receptacles, as the remaining snap-in elements remain in a non-engaged position. In this state, the clutch segment that supports the position-varying device segment may be manually returned to the initial state. The force and/or torque, which is needed to move back into the initial state, is considerably less than the force or torque, by which the overload and the decoupling of the two clutch segments was produced.

In one embodiment, the snap-in elements and the snap-in receptacles may be arranged according to prime number distances on a segment of the periphery, where several equally sized peripheral segments are provided. The arrangement of the snap-in elements may repeat at regular intervals. This repetition of the snap-in element positions enables the course of the force or torque to be influenced back into the initial position with a manual switching.

In another embodiment, a peripheral segment may include 180° or 120° or 90° or 60° or 45°. If a peripheral segment includes 90°, for example, the arrangement of the snap-in elements repeats four times around the periphery.

In one embodiment, four snap-in elements are arranged on a peripheral segment in the prime number distances 1*w, 2*w, 3*w and 5*w, where w=peripheral segment/n, and n corresponds to the total of the prime number distances. The prime number distances correspond to the smallest prime numbers 1, 2, 3, and 5, using which the distances of the snap-in elements are defined. Four snap-in elements may be arranged on a peripheral segment at the positions 1*w, 3*w, 6*w and 11*w. These positions result from the total of the prime number distances (i.e., the total of the position differences). The distances (differences) of the positions are prime numbers.

In order to influence the course of the force or torque during manual switching of the overload clutch of the medical device, at least one prime number position may be vacant for the snap-in elements. In this way, the switching performance may be individually influenced in order to optimize the manual actuation and thus the switching back into the initial state.

In one embodiment, the snap-in elements may be spring-loaded and embodied as pins or bolts that engage in the snap-in receptacles.

In one embodiment, the position-varying device segment may be embodied as a C-arm.

DETAILED DESCRIPTION OF THE DRAWINGS

Figure 1:
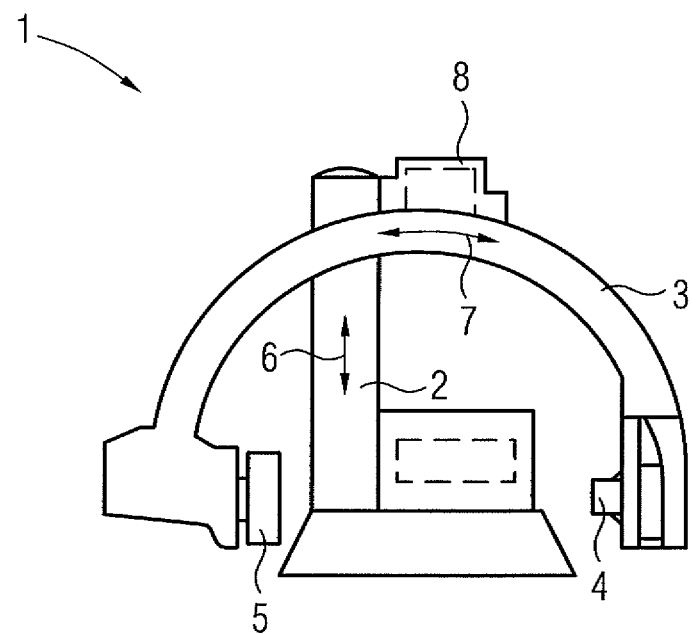
FIG. 1 shows one embodiment of a medical device.

A medical device 1 shown in FIG. 1 is embodied as an X-ray device and includes a C-arm 3 arranged on a support arm 2 as a position-varying device segment. The C-arm 3 supports an x-ray source 4 at one end, and an X-ray detector 5 is arranged on an opposing end of the C-arm 3. The C-arm 3 may be vertically displaced along the double arrow 6. The C-arm 3 may also implement a rotational movement along the double arrow 7.

The medical device 1 includes an electric drive 8 at an upper end of the support arm 2. The electric drive 8 is connected to the C-arm 3 by way of a gear unit. A mechanical drive chain is thus formed by the electric drive 8 and the gear unit, which is not visible in FIG. 1.

The C-arm 3 is connected to the mechanical drive chain using an overload clutch. A mechanical overload may occur, for example, if an obstacle is located in a movement range of the C-arm 3, towards which obstacle the C-arm 3 is pivoted. In order to avoid damage to the electric drive 8 of the gear unit, the overload clutch is moved out of an initial state into a decoupled state, as a result of which a force transmission from the mechanical drive chain to the position-varying device segment (e.g., the C-arm 3) is interrupted. In an overload instance of this type, the electric drive may be switched off for safety reasons. In addition, a braking apparatus may bring the movement of the C-arm 3 to a halt.

Figure 2:
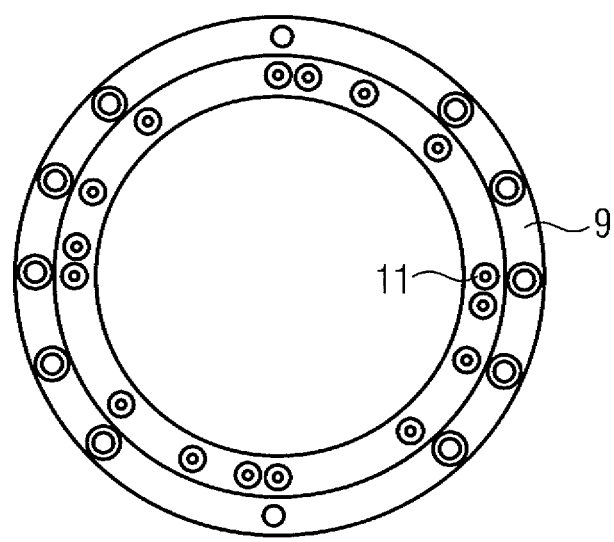
FIG. 2 shows one embodiment of a clutch segment with snap-in receptacles.
Figure 3:
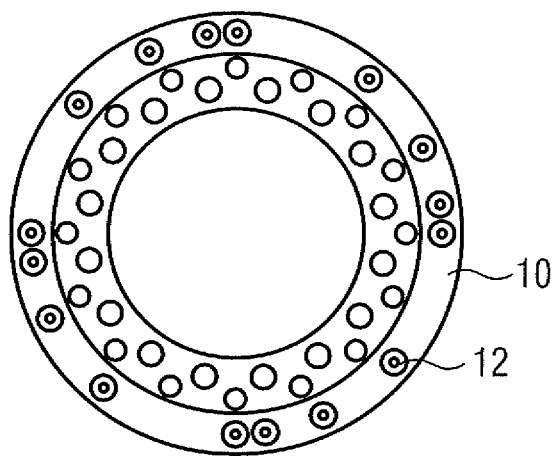
FIG. 3 shows one embodiment of a clutch segment with snap-in elements.

FIGS. 2 and 3 show components of the overload clutch. The components may include, for example, a clutch segment 9 with snap-in receptacles in FIG. 2 and a clutch segment 10 (e.g., a coupling segment) with snap-in elements in FIG. 3 (e.g., two clutch segments). The two clutch segments 9, 10 are embodied annularly. One clutch segment of the two clutch segments 9, 10 is fixedly connected to the mechanical drive chain of the medical device 1. The other clutch segment of the two clutch segments 9, 10 is fixedly connected to the position-varying device segment (e.g., the C-arm 3). Each of the two clutch segments 9, 10 includes a plurality of holes that are distributed across the periphery, the plurality of holes being used to fasten the clutch segment 9, 10 to the mechanical drive chain and/or the C-arm 3. The clutch segment 9 includes a plurality of snap-in receptacles 11 that are distributed across the periphery, the snap-in receptacles 11 being embodied as tapped blind holes in the exemplary embodiment shown in FIG. 2. In other embodiments, snap-in receptacles may also be embodied as clearance holes. The coupling segment 10 includes a plurality of snap-in elements 12 that are distributed across the periphery, the snap-in elements extending at right angles to a plane spanned by the clutch segment 10 in an axial direction. The snap-in elements 12 are embodied as spring-loaded, and each of the snap-in elements 12 includes an axially moveable bolt that is impinged by a pretensioned spring. When applying a force that is directed in an opposite direction to the spring force, the bolt is moved with respect to the clutch segment 10.

The snap-in receptacles 11 in the clutch segment 9 and the snap-in elements 12 in the clutch segment 10 are embodied and arranged such that the snap-in elements 12 and the snap-in receptacles 11 engage in one another in an initial state so that a transmission of a torque from the mechanical drive chain to the C-arm 3 may be provided. In the event of an overload, however, the snap-in elements 12 disengage from the snap-in receptacles 11, as a result of which the torque transmission is interrupted.

As shown in FIGS. 2 and 3, the snap-in receptacles 11 and the snap-in elements 12 are irregularly distributed over the periphery of the clutch segments 9, 10.

Figure 4:
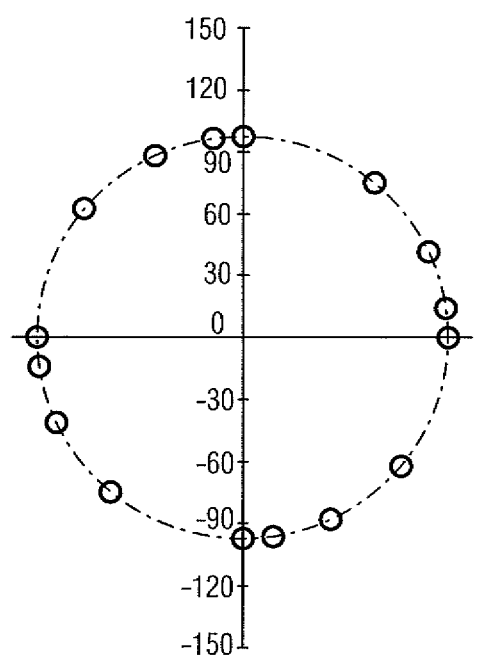
FIG. 4 shows a representation of one embodiment of the arrangement of the snap-in receptacle.

The arrangement of the snap-in receptacles and/or the snap-in elements is shown in FIG. 4. The snap-in elements 12 and the associated snap-in receptacles 11 are each arranged according to prime number distances on a segment of the periphery. Several equally-sized peripheral segments are provided. In the exemplary embodiment shown, four peripheral segments are provided. In one embodiment, each of the four peripheral segments covers a range of 90°. The snap-in elements 12 and the snap-in receptacles 11 are arranged according to prime number distances. The lowest prime numbers are 1, 2, 3, 5 and 7. If the prime number distances are determined accordingly, prime number positions 1*w, 3*w, 6*w, and 11*w are obtained. w corresponds to the peripheral segment/n, where n corresponds to a total of the prime number distances. In the exemplary embodiment shown, n=1+2+3+5 and w=90°/11. The snap-in elements 12 are therefore found at the following positions: 0°, 8.1°, 24.5° and 49.1°.

In other words, a peripheral segment is divided into n identical parts, where n is a prime number. If, as in this embodiment, n=11 is selected, a part of the peripheral segment is produced by 90°/11=8.182°. A start of a division segment at the peripheral segment (e.g., reference circle) may be referred to as a position that is counted upwards from 0 in a positive mathematical sense (e.g., up to 10), where a position 11 corresponds to a position 0 of the following peripheral segment. The positions are defined as snap-in positions that begin with 0 and have a monotonously increasing prime number distance (e.g., 1, 2, 3, 5) with respect to a precursor, respectively.

The arrangement repeats four times along the periphery of the coupling element. This irregular distribution of the snap-in receptacles and the snap-in elements provides that in the initial state, all sixteen snap-in elements are in the corresponding snap-in receptacles. If, in the event of an overload, the overload clutch is decoupled, the snap-in elements engage in next positions following a rotation of 8.1°. However, only four of the sixteen snap-in elements engage, the remaining snap-in elements slide over a corresponding counter face of the other clutch segment. This results in the C-arm being easily manually moved back into the initial position, since only the friction and resistance of the four snap-in elements is to be overcome and not that of sixteen snap-in elements, as is provided from the initial position.

Figure 5:
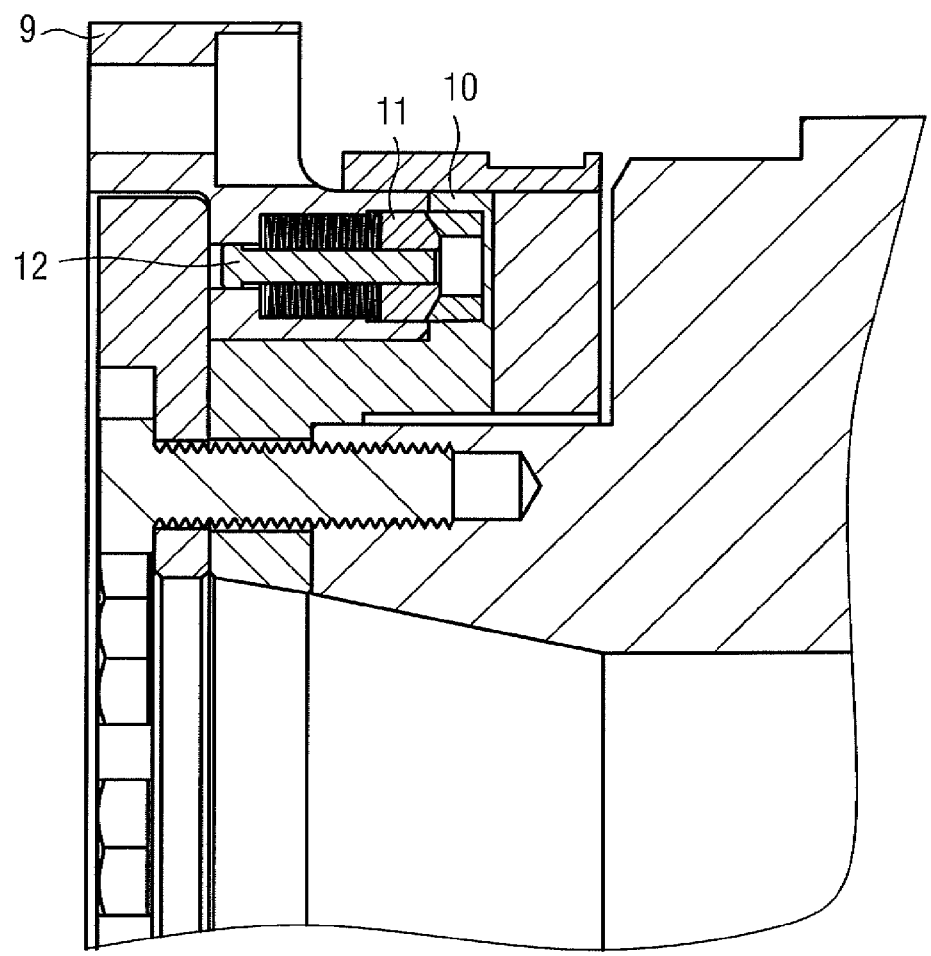
FIG. 5 shows a cut-away side view of one embodiment of the overload clutch.

FIG. 5 shows a cut-away side view of one embodiment of the coupling elements 9, 10 in the assembled state.

Figure 6:
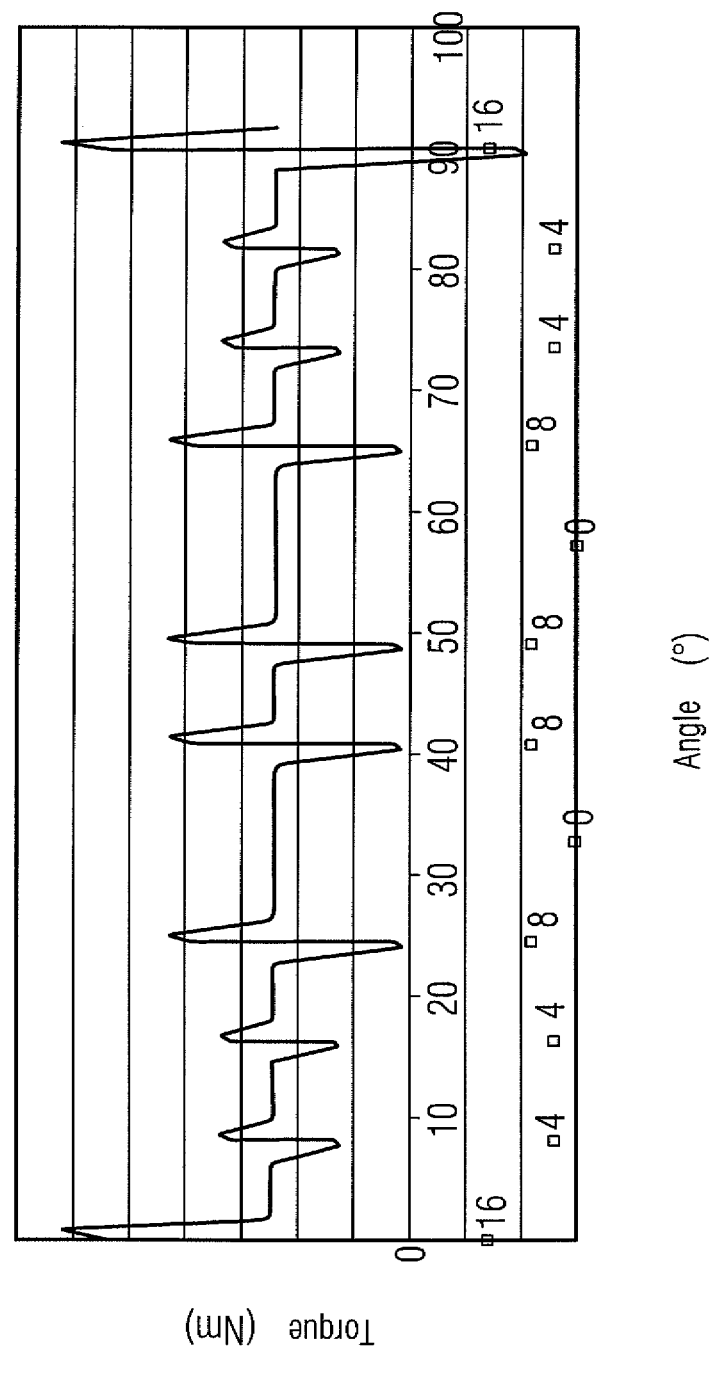
FIG. 6 shows the path of the torque in the case of a decoupled overload clutch of FIG. 5.

FIG. 6 shows a graph of torque plotted against an angle of rotation. A very high torque is initially needed from the initial state in order to effect activation of the overload clutch. After decoupling, the torque returns to a lower value, which is approximately half as large as the maximum value when triggering the overload clutch. If the snap-in elements in a next position are engaged into the snap-in receptacles following a rotation of approximately 8.1°, only a minimal torque is needed in order to return the C-arm 3 to the initial position. This lower torque amounts to approximately one quarter of the maximum torque that develops when triggering the overload clutch.

A total number of simultaneously engaged snap-in elements is specified in a lower region in FIG. 6. The total number of engaged elements fluctuates between 16 (e.g., all snap-in elements engaged) and 0 (e.g., no snap-in element engaged). If four snap-in elements are engaged, one snap-in element is engaged per peripheral segment in each instance. The total torque that is to be expended in order to overcome the engaged snap-in position is composed of a constant friction torque and a dependent torque, which depends on the number of engaging snap-in elements. The constant friction torque provides that the position-varying device segment is still retained when all snap-in elements are disengaged, thereby preventing slipping.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical device comprising:
a position-varying device segment;
an electric drive for positioning the position-varying device segment;
a mechanical drive chain; a gear unit and an overload clutch arranged along the mechanical drive chain between the electric drive and the position-varying device segment; and
snap-in elements arranged on a clutch segment of the overload clutch, the snap-in elements engaging in snap-in receptacles of another clutch segment of the overload clutch,
wherein the snap-in elements and the snap-in receptacles are distributed irregularly,
wherein the snap-in elements and the snap-in receptacles are arranged according to prime number distances on a segment of the periphery, and wherein the periphery comprises a plurality of equally-sized peripheral segments.

2. The medical device as claimed in claim 1, wherein a peripheral segment of the plurality of equally-sized peripheral segments comprises 180°, 120°, 90°, 60°, or 45° of the peripheral.

3. The medical device as claimed in claim 2, wherein the snap-in elements comprise four snap-in elements, and the snap-in receptacles comprise four snap-in receptacles, and
wherein the four snap-in elements and the four snap-in receptacles are arranged on a peripheral segment of the periphery in prime number distances 1*w, 2*w, 3*w and 5*w, w being the peripheral segment/n and n being a total of the prime number distances.

4. The medical device as claimed in claim 2, wherein at least one of the prime number positions is vacant for the snap-in elements and snap-in receptacles.

5. The medical device as claimed in claim 1, wherein the snap-in elements comprise four snap-in elements, and the snap-in receptacles comprise four snap-in receptacles, and
wherein the four snap-in elements and the four snap-in receptacles are arranged on a peripheral segment of the periphery in prime number distances 1*w, 2*w, 3*w and 5*w, w being the peripheral segment/n and n being a total of the prime number distances.

6. The medical device as claimed in claim 5, wherein the distribution of the snap-in elements and snap-in receptacles repeats on each peripheral segment of the plurality of peripheral segments.

7. The medical device as claimed in claim 6, wherein at least one of the prime number positions is vacant for the snap-in elements and snap-in receptacles.

8. The medical device as claimed in claim 1, wherein the snap-in elements comprise four snap-in elements, and the snap-in receptacles comprise four snap-in receptacles, and
wherein the four snap-in elements and the four snap-in receptacles are arranged on a peripheral segment of the periphery in prime number distances 1*w, 3*w, 6*w and 11*w, w being the peripheral segment/n and n being a total of the prime number distances.

9. The medical device as claimed in claim 8, wherein at least one of the prime number positions is vacant for the snap-in elements and snap-in receptacles.

10. The medical device as claimed in claim 8, wherein the snap-in elements are spring-loaded.

11. The medical device as claimed in claim 8, wherein the position-varying device segment is configured as a C-arm.

12. The medical device as claimed in claim 1, wherein at least one of the prime number positions is vacant for the snap-in elements and snap-in receptacles.

13. The medical device as claimed in claim 12, wherein the snap-in elements are spring-loaded.

14. The medical device as claimed in claim 1, wherein the snap-in elements are spring-loaded.

15. The medical device as claimed in claim 14, wherein the snap-in elements are configured as pins or bolts that engage in the corresponding snap-in receptacles configured as recesses.

16. The medical device as claimed in claim 1, wherein the position-varying device segment is configured as a C-arm.

17. The medical device as claimed in claim 1, wherein the snap-in elements are spring-loaded.

18. The medical device as claimed in claim 1, wherein the position-varying device segment is configured as a C-arm.

* * * * *